(12) United States Patent
Potvin

(10) Patent No.: US 6,502,789 B2
(45) Date of Patent: Jan. 7, 2003

(54) FLEXIBLE KITE

(76) Inventor: Raymond Potvin, 3-C St. Jean-Baptiste, Valley Field, 9C (CA), J6T 1Y9

( * ) Notice: Subject to any disclaimer, the term of this patent is extended or adjusted under 35 U.S.C. 154(b) by 0 days.

(21) Appl. No.: 09/775,111

(22) Filed: Feb. 1, 2001

(65) Prior Publication Data

US 2002/0020784 A1 Feb. 21, 2002

(51) Int. Cl.⁷ .............................................. B64C 31/06
(52) U.S. Cl. ............................ 244/153 R; 114/102.11
(58) Field of Search ....................... 244/153 R, 155 A, 244/142, 145, 152, DIG. 1; 280/810; 114/39.12, 39.13, 102.1, 102.11, 102.16, 102.18

(56) References Cited

U.S. PATENT DOCUMENTS

| | | | | |
|---|---|---|---|---|
| 3,358,399 A | * | 12/1967 | Waldmann | 244/153 R |
| 3,448,864 A | * | 6/1969 | Fenn et al. | 212/71 |
| 4,129,272 A | * | 12/1978 | Jones et al. | 244/145 |
| 4,461,438 A | * | 7/1984 | Pook et al. | 244/153 R |
| 5,120,006 A | * | 6/1992 | Hadzicki | 244/153 R |
| 6,145,789 A | * | 11/2000 | Matlin et al. | 244/153 R |

FOREIGN PATENT DOCUMENTS

DE    2737597 A1  *  3/1978  ........... B64C/31/06

* cited by examiner

Primary Examiner—Robert P. Swiatek
Assistant Examiner—Timothy D Collins

(57) ABSTRACT

A spoon shaped simple skin kite for kite sailing having a long flexible fiberglass rod on the leading edge as the only structure, many bridles that are all connected directly to that rod, no lines a 30 inches long straight handle to steer it that turns around the same axis as the kite turns.

2 Claims, 1 Drawing Sheet

FLEXIBLE KITE

BACKGROUND

Figure 1:
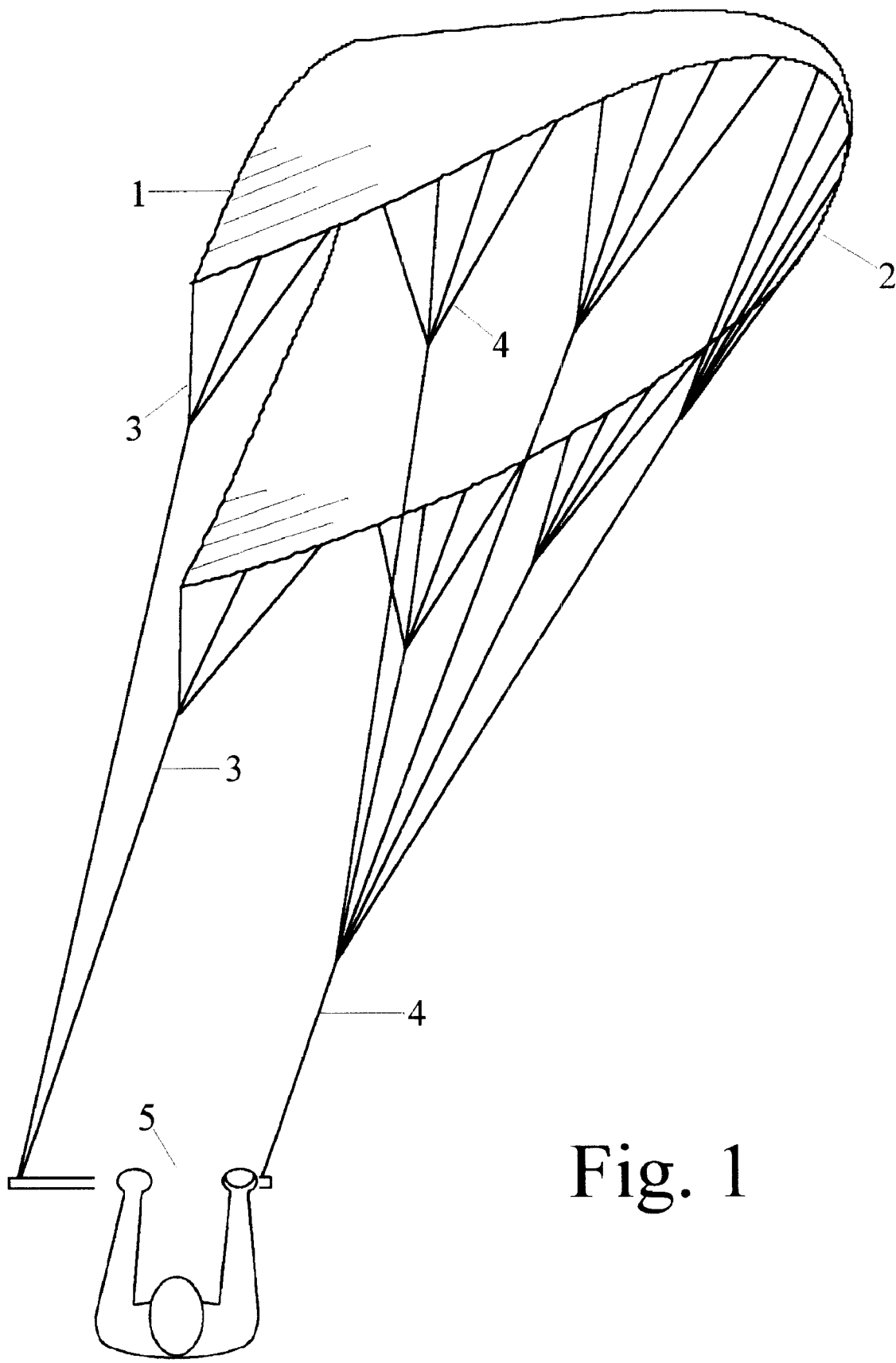

The present invention relates to "traction kites" or "power kites" designed for sailing with different vehicles like skis, skates, surfboards, buggies.

These kites derive from "acrobatic kites" with two lines that can be steered by pulling on one or the other line, they are simply bigger and more powerfull but steer the same way. Because of their long lines 100 feet long they are complex to use, cumbersome and dangerous because the kite is far away from the user and can have considerable radial accelerations. On the field the long lines, which can count up to four, can become very cumbersome when there are many users around and can tangle very badly.

Present kite has no lines therefore has a lot less radial acceleration than others what renders it clearly safer to use. It's bridles are connected directly to a straight handle 30 inches long. Said handle steers the kite revolving on the same axis as the kite itself, a simpler and more natural steering movement but unefficient with long lines.

Power kites can have different structures:
1. With cells, like parachutes, double skin connected by walls and many row of bridles: they are the most common.
2. With pressure inflated tubes, without bridles: they are specifically designed to be used on water. U.S. Pat. No. 4,780,078 Legaignoux).
3. With fiberglass rods, single skin and many rows of bridles: their transverse rods renders them fragile.
4. With cells, without bridles: they are also designed to be used on water.
5. Present kite has a single skin and a long fiberglass rod on the leading edge as the only structure. It has bridles that are all connected to the leading edge. That kind of structure takes a half spoon like shape when it si inflated. Such a shape is easier to inflate and collapses less easily than others, which facilitates the handling. When it hits the ground it bends without breaking because of it's flexibility.

Because of those particularities present kite allows beginners to sail in minutes instead of having to fly a small kite for hours before switching to a bigger one and trying to moove around without being catapulted because of the redial acceleration of the kite. It is easy to make and to repair and it's power compare to others.

SUMMARY

To sail with a kite one has to be able to steer it, to launch it and to land it easily from far away. That type of "power kites" derive from the "acrobatic kites" and has two three or four lines about 100 feet long to steer it. When such a kite is flying it can moove at considerable radial speed developing an enormous instant power which can hurt it's user. Moreover the lines can become very cumbersome when there is a lot of kites at the same spot and they can sometimes get tangled very badly.

Present kite avoids these problems by being closer to the user, but the steering mode used with long lines does not work as good when we take them off. I found a very efficient way to steer a kite whose lines were taken off that works with all "power kites", but I also found a new kite structure more efficient than others for that kind of use: it inflates and deflates to will more easily, collapses less easily in whirlwind, is easier to handle an to make than others. It does not turn as well as others with long lines but works better than others with no lines.

DRAWINGS

FIG. 1 is a perspective view of an inflated kite showing the spoon like shape of the skin 1, the leading edge rod 2; the two rear group of bridles 3, the front group of bridles 4, the handle 5 and the user 6.

DESCRIPTION

Present invention is a kite designed for sailing, inflated it has a spoon like shape 1, spread openned it forms a half circle. Its only structure is a 24 feet long fiberglass rod 2 so flexible it is stored rolled in circles 3 feet in diameter. When it hits the ground it bends without breaking.

About 25 bridles, regularly spaced, are tied to the rod on one of their ends and divided in three groups, two rear groups 3 and one front group 4. At lest the least bridles on each side must be part of the rear groups. Shown kite has three. Bridles are then joined together on their other end and connected to a 30 inches long straight handle 5 by means of longer bridles, rear groups at one end of the handle and front group at the other end. User 6 can then change pitch and direction of the kite by changing the respective pitch and direction of the handle.

What is claimed is:
1. A kite for sailing comprising:
   a single layer skin with the only supporting structure being a flexible fiberglass rod or tube located at the leading edge, the flexible fiberglass rod or tube being connected to a first trailing edge continuing to the leading edge and returning continuously to a second trailing edge opposite to the first trailing edge, two rear groups and one front group of bridles being directly connected to the flexible fiberglass rod or tube, the group of bridles also being directly connected to a straight handle at two points, the front group of bridles connected at one end and the two rear groups of bridles connected at the opposite end.
2. The kite of claim 1, wherein the handle steers the kite by revolving on a plane at right angle with an axis going from the kite to the handle, instead of revolving on a plane passing by said axis.

* * * * *